United States Patent
Park et al.

(10) Patent No.: US 7,212,861 B1
(45) Date of Patent: May 1, 2007

(54) MONITORING VENTRICULAR CONTRACTIONS USING AN IMPLANTABLE STIMULATION DEVICE

(75) Inventors: Euljoon Park, Valencia, CA (US); Gene A. Bornzin, Simi Valley, CA (US); Robert G. Turcott, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 401 days.

(21) Appl. No.: 10/838,939

(22) Filed: May 3, 2004

(51) Int. Cl.
*A61N 1/00* (2006.01)

(52) U.S. Cl. .......................... 607/17; 607/18; 607/19; 600/486

(58) Field of Classification Search ................ 600/486; 607/17–19
See application file for complete search history.

(56) References Cited

U.S. PATENT DOCUMENTS

| | | | |
|---|---|---|---|
| 5,300,093 A | 4/1994 | Koestner et al. | 607/32 |
| 5,417,717 A | 5/1995 | Salo et al. | 607/18 |
| 6,070,100 A | 5/2000 | Bakels et al. | 607/9 |
| 6,223,082 B1 | 4/2001 | Bakels et al. | 607/17 |
| 6,280,389 B1 * | 8/2001 | Ding et al. | 600/485 |
| 6,738,667 B2 * | 5/2004 | Deno et al. | 607/23 |
| 6,754,530 B2 | 6/2004 | Bakels et al. | 607/14 |
| 2002/0143368 A1 | 10/2002 | Bakels et al. | 607/9 |

\* cited by examiner

*Primary Examiner*—Robert E. Pezzuto
*Assistant Examiner*—Brian T. Gedeon

(57) ABSTRACT

An implantable cardiac stimulation device is configured to measure selected ventricular contraction parameters and possibly apply stimulation therapy based on the ventricular contraction parameters. In accordance with one aspect, the ventricular contraction parameters include impedance values that correspond to the volume of fluid in the right ventricle and the left ventricle. In accordance with another aspect, the ventricular contraction parameters include motion values that correspond to heart sounds/motion in the right ventricle and the left ventricle. The ventricular contraction parameters can be used to form pseudo P-V loop from which treatment decisions can be made.

18 Claims, 10 Drawing Sheets

MONITORING VENTRICULAR CONTRACTIONS USING AN IMPLANTABLE STIMULATION DEVICE

RELATED PATENT APPLICATIONS

This application is related to U.S. patent applications: Ser. No. 10/838,947, titled "Monitoring Ventricular Contractions Using an Implantable Stimulation Device"; and Ser. No. 10/838,692, titled "Monitoring and Synchronizing Ventricular Contractions Using an Implantable Stimulation Device", filed May 3, 2004, and which are incorporated herein in their entirety by reference.

TECHNICAL FIELD

Exemplary methods and apparatuses presented herein generally relate to cardiac pacing devices and more particularly for generating useful pseudo pressure-volume loop information about one or both ventricles that can be used to analyze/monitor a patient's cardiac condition and apply/adjust stimulation therapy.

BACKGROUND

Congestive heart failure (CHF) is a disease condition that involves the loss of pumping ability by the heart. Often CHF is accompanied by fluid accumulation in the body tissues, and especially in the lungs. CHF usually develops slowly, such that symptoms may not appear until the condition has progressed over time. This is because the heart deals with and essentially hides the underlying problems by making adjustments that delay—but do not prevent—the eventual loss in pumping capacity. For example, the heart may cope with and hide the effects of CHF by enlarging (i.e., dilatation) to allow more blood to enter into the heart. The muscle fibers of the heart may also thicken (i.e., hypertrophy) to strengthen the heart muscle and thereby contract more forcefully and pump more blood. The heart may also beat more often to increase circulation. By making these adjustments, or compensating, the heart can temporarily make up for losses in pumping ability, sometimes for years. However, compensation has its limits. Eventually, the heart cannot offset the lost ability to pump blood, and the signs of CHF will appear.

Traditionally, a patient afflicted with CHF would receive drug therapy and make healthy lifestyle changes. Recently, there has been a movement towards further treating certain CHF patients with pacing therapy. Here, it has been found that the contractions of the left ventricle and the right ventricle may become unsynchronized, for example, as a result of a bundle branch block. This loss of synchronization between the left and right ventricles can significantly reduce the heart's pumping ability. Implantable pacing devices can be configured to apply therapy (e.g., bi-ventricular pacing) to selected areas of the heart to improve the heart's pumping ability. However, before shock therapy can be applied, there is a need to determine the applicable pacing parameters for the patient.

U.S. Pat. No. 6,280,389, issued to Ding et al., titled "Patient Identification for the Pacing Therapy Using RV-LV Pressure Loop," teaches that not all CHF patients may benefit from pacing therapy. Here, for example, Ding et al. provide methods for determining if a CHF patient may benefit from pacing therapy based on measured pressure levels within the left ventricle (LV) and right ventricle (RV). The measured pressure level data can be plotted to form a loop. Based on this RV-LV pressure loop, it can be determined whether a CHF patient should receive pacing therapy.

Another useful data set is a ventricle's pressure and volume, which also forms a loop during a cardiac cycle. The resulting pressure-volume (P-V) loop can be used to diagnose and treat deceases, such as CHF.

Measuring the pressure within the RV and/or LV can be accomplished during acute treatment, for example, within a hospital setting wherein catheters having leads with pressure sensors may be placed within each ventricular chamber. However, such sensors may not be suited for chronic diagnostics and treatment using an implantable device. There is significant trepidation in placing leads within the LV during chronic treatment, since the blood pressure within this chamber is much higher compared to the RV. There is a danger, should a lead break within the LV, that the broken piece(s) may flow with the blood to the patient's brain and cause a stroke.

Consequently, there is a need for methods and apparatuses that can generate P-V-like loops (e.g., pseudo P-V loops) for the right and/or left ventricles, which can then be used to analyze/monitor a patient's cardiac condition and selectively apply/adjust stimulation-based pacing therapy. Preferably, the methods and apparatuses can be employed within implantable devices used for chronic treatment of CHF and/or other heart diseases.

SUMMARY

Methods and apparatuses are provided which generate P-V-like curve information (e.g., pseudo P-V loops) for one or both ventricles, which can then be used to analyze/monitor a patient's cardiac condition and/or apply/adjust stimulation therapy. The methods and apparatuses can be advantageously employed within implantable devices that are used for chronic treatment of CHF and/or other heart diseases/conditions.

Thus, for example, in accordance with certain implementations, a method is provided for use with an implantable cardiac stimulation device. The method includes collecting ventricle motion data associated with at least one ventricle in a heart during at least one cardiac cycle and also collecting ventricle impedance data associated with the ventricle during the cardiac cycle. Then, the method includes processing the collected motion and impedance data to produce corresponding motion-impedance curve data that is associated with the ventricle. This motion-impedance curve data may take the form of a motion-impedance loop that is essentially a pseudo P-V loop.

In accordance with other exemplary implementations, a pseudo P-V loop may be generated by considering collected pressure data and impedance data for a ventricle. Here, for example, a pressure-impedance loop may be generated, which is essentially a P-V loop. In accordance with other exemplary implementations, a pseudo P-V loop may also be generated by considering collected photoplethysmography data, alone or in combination with motion, impedance, and pressure data. Here, for example, a pressure-plethysmogram loop may be generated, which is essentially a P-V loop.

The resulting pseudo P-V loop information from these various exemplary implementations may then be used to apply/adjust stimulation therapy associated with the ventricle(s) and/or otherwise reported out to the patient/physician for further consideration.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

The methods and apparatuses provided herein allow a pseudo P-V loop (or curve) and/or related information to be gathered for one or both of the ventricles using currently available leads and sensing devices.

In accordance with certain aspects, the pseudo P-V loop information may include motion information that is correlated to ventricular pressure and/or impedance information that is correlated to ventricular volume.

Thus, for example, in accordance with certain implementations the pseudo P-V loop takes the form of a motion-impedance loop, while in other implementations the pseudo P-V loop takes the form of a pressure-impedance loop. The motion-impedance loop may be advantageous when monitoring the left ventricle, since the motion-impedance loop does not require the use of a lead within the left ventricle. Additionally, both of these implementations alleviate the need to directly measure volume within the ventricle chamber, which often proves difficult for an implanted device providing long term chronic treatment/monitoring.

The motion-impedance loop information that is generated takes advantage of the correlation between the pressure changes within the ventricle and detectable heart sounds/vibrations associated with the closing/opening of valves (e.g., the mitral valve in the left ventricle) and other movements of the ventricle during the cardiac cycle. There is also a correlation between the volume of blood within the chamber of the ventricle and the impedance associated with a conductive path through the ventricle and in particular the blood within the chamber of the ventricle. Hence, as would a traditional P-V loop be used, the P-V loops provided herein can be used to analyze the pumping activity of one or both ventricles and make any necessary treatment decisions.

Exemplary Stimulation Device

The techniques described below are intended to be implemented in connection with any stimulation device that is configured or configurable to stimulate or shock a patient's heart. While the examples described below illustrate implantable stimulation devices with three leads having various components, it should be understood that the techniques herein can be applied to devices having one or more leads, and the lead(s) in certain implementations may be unipolar.

Figure 1A:
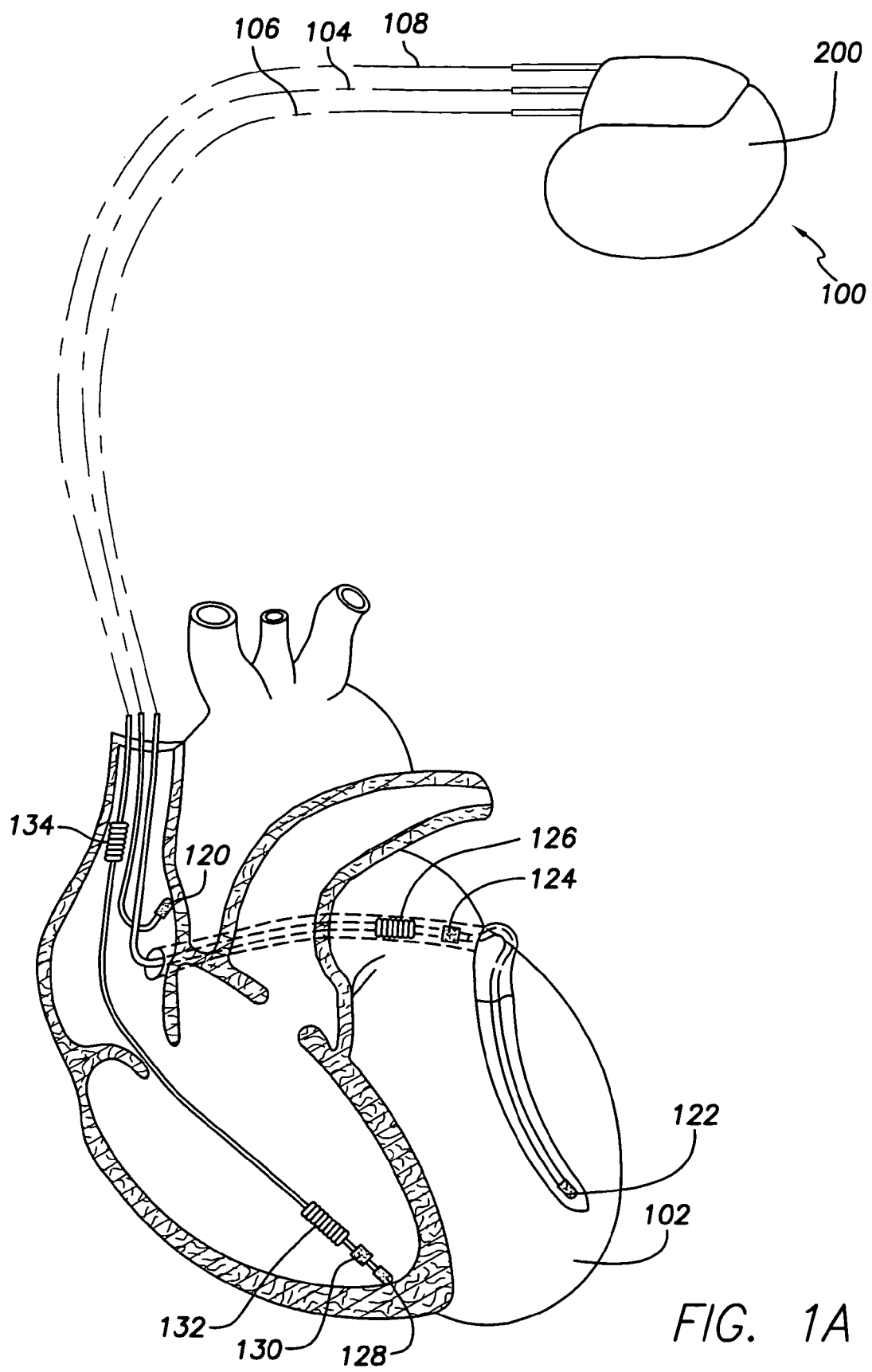
FIGS. 1A and 1B are simplified diagrams illustrating illustrative embodiments of an implantable stimulation device that is configured to detect ventricular contractions based on measured motion and impedance values and selectively apply responsive pacing therapy and/or report such information for further consideration by a physician, in accordance with certain exemplary implementations.

With this in mind, FIG. 1A shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the LV and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least an LV tip electrode 122, left atrial pacing therapy using at least a left atrial ring electrode 124, and shocking therapy using at least a left atrial coil electrode 126.

Stimulation device 100 is also shown in electrical communication with the patient's heart 102 by way of an implantable RV lead 108 having, in this implementation, a RV tip electrode 128, a RV ring electrode/sensor 130, an RV coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, RV lead 108 is capable of receiving cardiac signals, and delivering stimulation in the form of pacing and shock therapy to the right ventricle.

In accordance with certain aspects, stimulation device 100 can be configured to measure impedance values (e.g., data) for one or both of the ventricles. Preferably, multiple impedance values are collected over one or more cardiac cycles for the monitored ventricle(s). Each measured impedance value will be significantly correlated to the volume of blood present in the applicable ventricle at the time of measurement, as blood tends to provide a much better electrical conductor than the surrounding tissues. As a result, lower impedance values will be measured when a ventricle is full of blood (e.g., pre-ejection) and higher impedance values will be measured once the ventricle has contracted and ejected most of the blood. Thus, the measured impedance values are significantly correlated to the volume of blood within the ventricle.

To measure the impedance values for the right ventricle, for example, a known current can be passed between a device case or housing electrode (e.g., 100) and an electrode provided within the right ventricle, such as, a RV tip electrode 128, a RV ring electrode/sensor 130 or an RV coil electrode 132. Preferably, the case electrode and RV electrode will be positioned such that the intervening volume of pre-ejection blood in the RV will provide a significant conductive path for the known current signal. The voltage drop through the resulting conductive path(s) is measured. The measured impedance can then be determined by applying Ohm's law using the known current and measured voltage value.

Similarly, to measure the impedance values for the LV, a known current can be passed between an electrode within the RV and an electrode configured for the LV. Thus, for example, a known current can be passed between RV tip electrode 128 and LV tip electrode 122. Preferably, the RV and LV electrodes will be positioned such that the intervening volume of pre-ejection blood in the LV will provide a significant conductive path for the known current signal. Thus, as with the RV, the voltage drop through the resulting LV related conductive path is measured and the measured impedance determined by applying Ohm's law using the known current and measured voltage value.

Figure 1B:
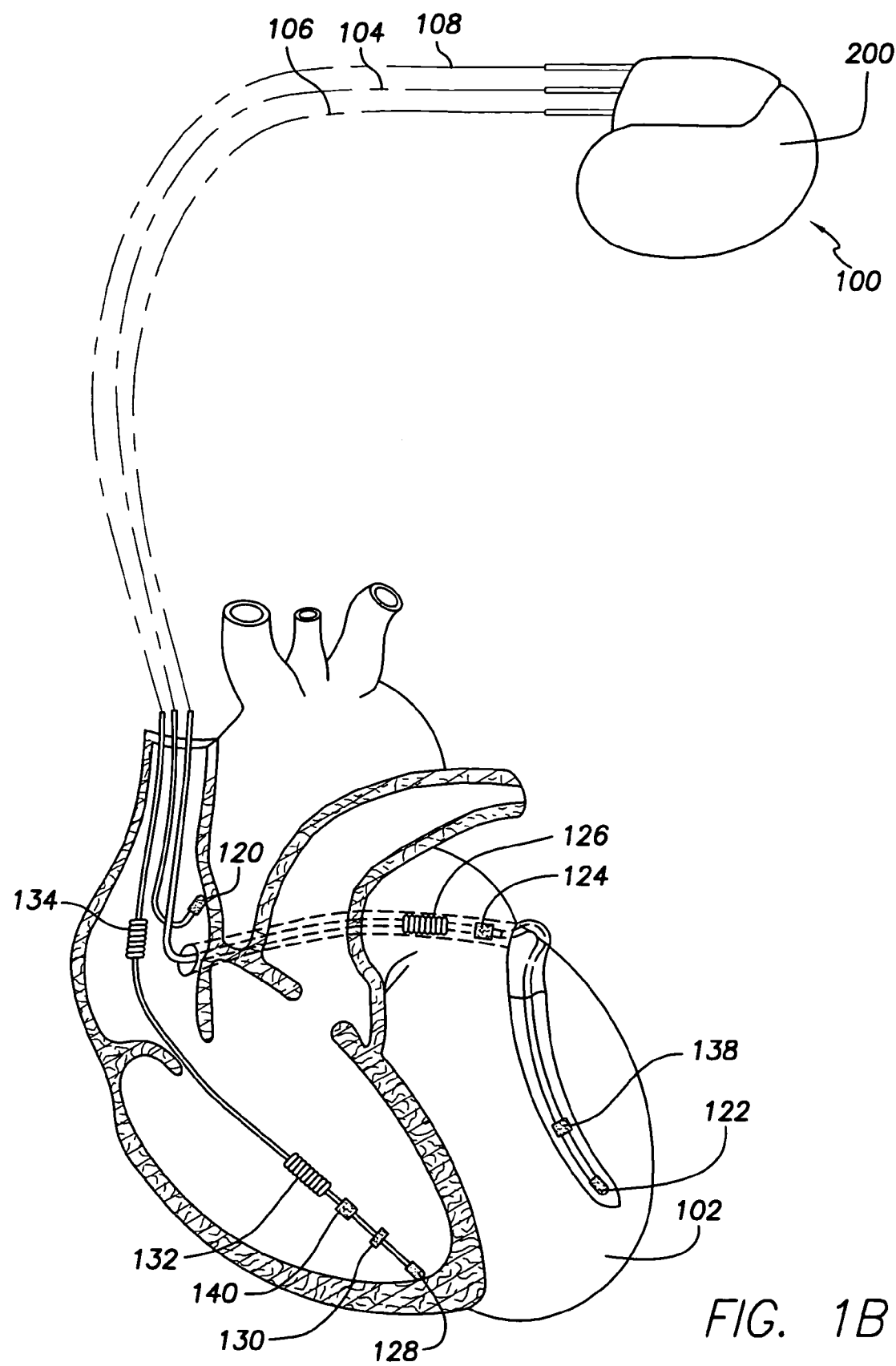

To support the gathering of motion data, in one exemplary implementation an LV accelerometer terminal ($V_L$ Accl) 205 and an RV accelerometer terminal ($V_R$ Accl) 215 are included in a switch matrix 226 (FIG. 2B) such that measured acceleration signals/values from LV motion sensor 138 and RV motion sensor 140 (FIG. 1B), respectively, can be received and processed, as described in more detail below.

Figure 2A:
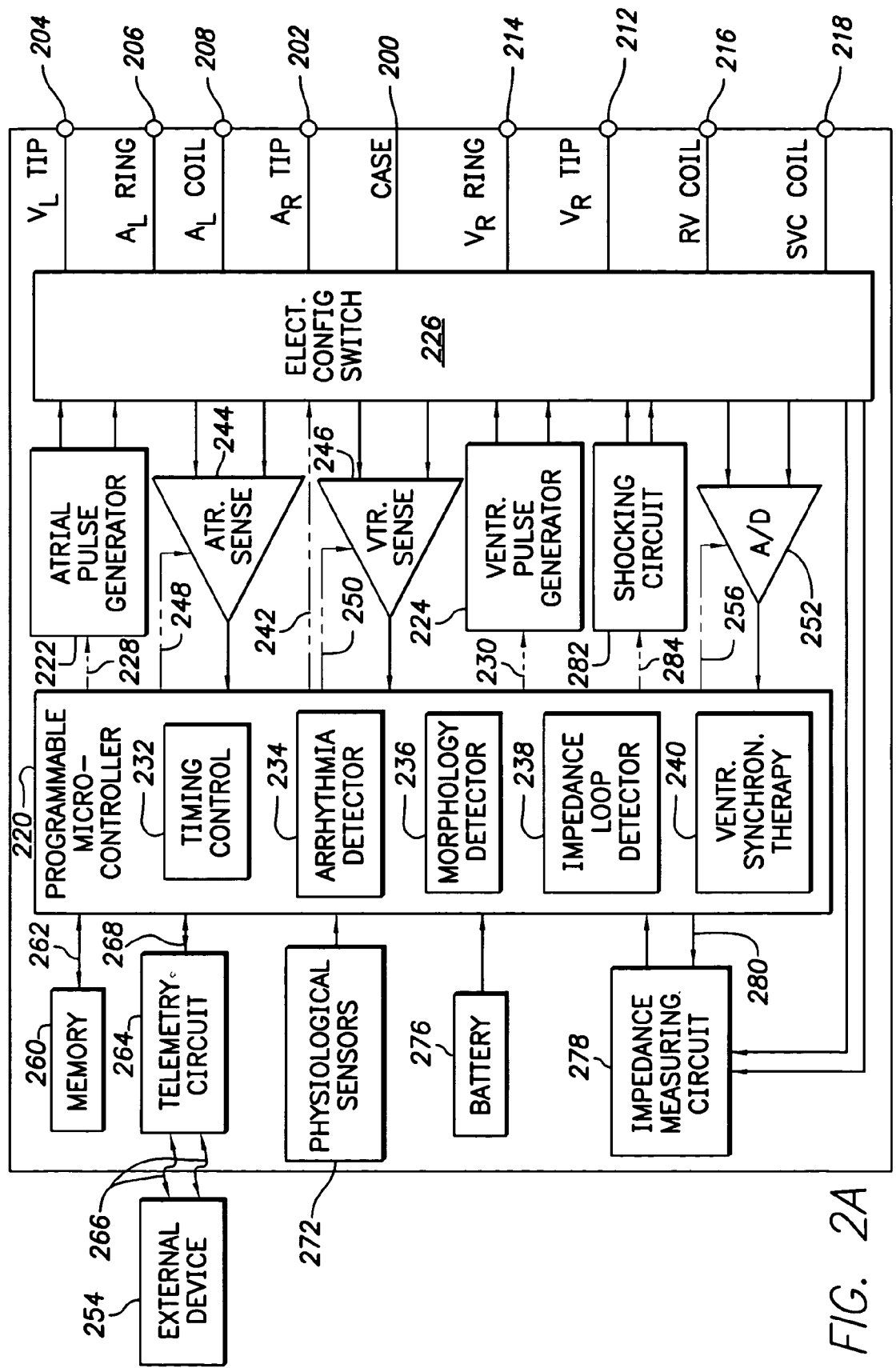
FIGS. 2A and 2B are functional block diagrams depicting selected features of an implantable stimulation device, for example, as in FIGS. 1A and 1B, in accordance with certain exemplary implementations.
Figure 2B:
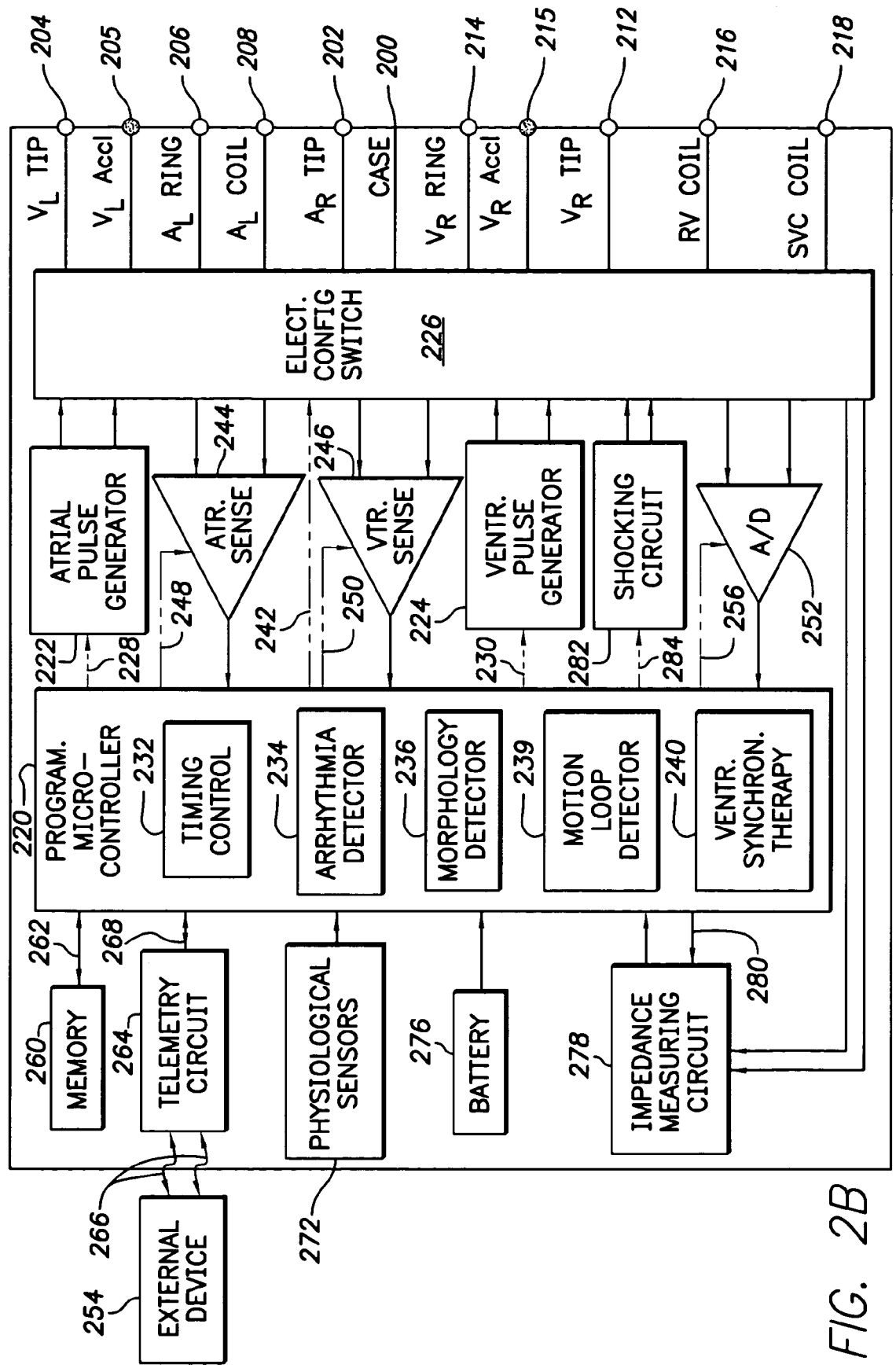

FIGS. 2A and 2B show exemplary, simplified block diagrams depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. A right atrial ring terminal ($A_R$ RING) may also be included adapted for connection to the atrial ring electrode 121. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the A/D converter 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 272, commonly referred to as a "rate-responsive" sensor because it is typically used to adjust pacing stimulation rate according to the exercise state of the patient. However, the physiological sensor 272 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses. While shown as being included within the stimulation device 100, it is to be understood that the physiologic sensor 272 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 272 optionally include sensors to help detect movement and minute ventilation in the patient. The physiological sensors 272 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Exemplary Cardiac Cycle

Figure 3:
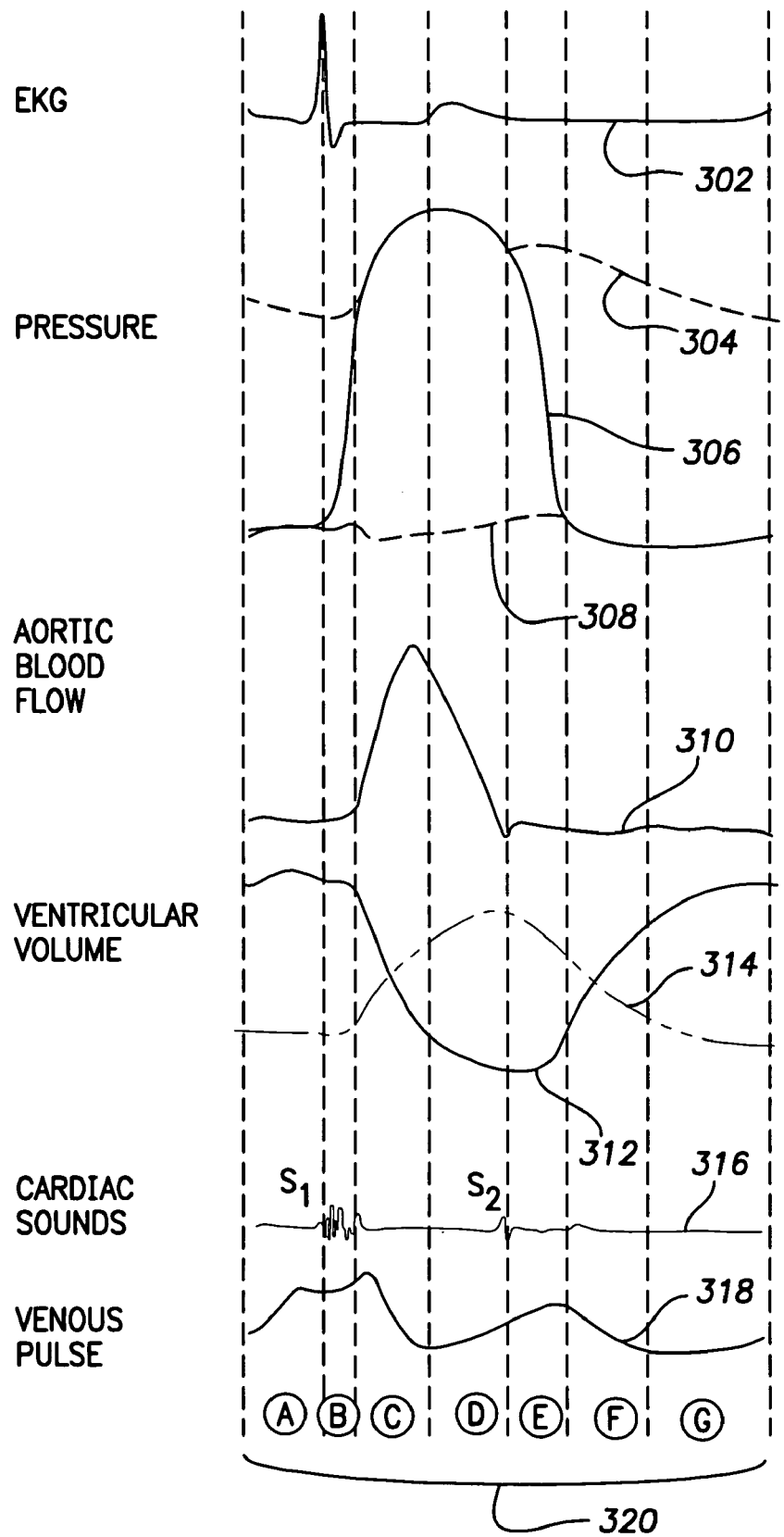
FIG. 3 depicts a collection of plotted values associated with cardiac activity, in accordance with certain exemplary implementations.

FIG. 3 depicts a collection of plotted values associated with cardiac activity, in accordance with certain exemplary implementations. Line 302, at the top of FIG. 3 shows the EKG signal for one cardiac cycle. Below it, line 304 shows the corresponding aortic pressure; line 306 shows the corresponding left ventricular pressure; and, line 308 shows the corresponding left atrial pressure.

Next, line 310 shows the aortic blood flow during the cardiac cycle. Line 312 shows the ventricular volume, which can be compared to line 306 to demonstrate that there is a correspondence between ventricular pressure and ventricular volume. Imposed over line 312, is a dashed line 314 that represents the amplitude of impedance values (e.g., a Z curve) measured using electrical signals passing through the left ventricle. As can be seen, there is an inverse proportional relationship between lines 312 and 314. Hence, there is a relationship between pressure, volume and measurable ventricular impedance.

Line 316 shows the corresponding cardiac sounds (i.e., a phonocardiogram), and in particular detectable $S_1$ and $S_2$ components relating to, in this example, the closing and opening, respectively, of the mitral valve during the cardiac cycle.

Finally, at the bottom of FIG. 3, line 318 shows the corresponding venous pulse.

Circled letters 320 are shown at the bottom of FIG. 3. These letters 320 illustrate certain the periods of the cardiac cycle as defined between dotted lines. Here, letter A marks an atrial systole period; letter B marks a period of isovolumic contraction; letter C marks a period of rapid ejection; letter D marks a period of reduced ejection; letter E marks a period of isovolumic relaxation; letter F marks a period of rapid ventricular filling; and, letter G marks a period of reduced ventricular filling diastasis.

Exemplary Traditional P-V Loop

Figure 4:
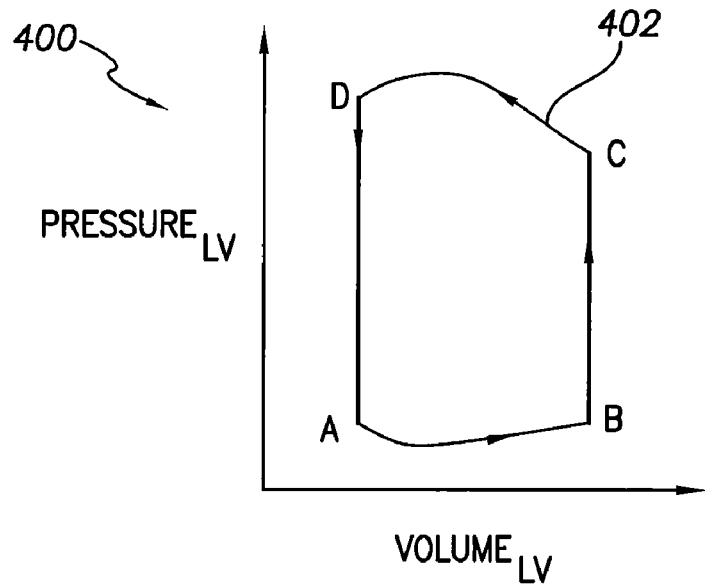
FIG. 4 is a graph depicting a conventional P-V loop for the left ventricle during a cardiac cycle.

FIG. 4 is a graph 400 depicting the pressure within a LV versus the volume of blood within the chamber of the LV during a cardiac cycle. The pressure-volume relationship is shown here as a P-V loop 402 by not considering the time element.

In this example, at point A on the P-V loop the mitral valve has opened and diastolic filling starts causing the volume to increase until point B is reached wherein the mitral valve closes. Next, isovolumic contraction occurs between points B and C, causing the pressure to increase. At point C, the aortic valve opens and ejection of the blood from the chamber of the left ventricle begins. This causes the volume to decrease and the pressure to increase for awhile and then to fall off. At point D, with most of the blood ejected from the chamber, the aortic valve closes once again. From point D to point A, isovolumic relaxation occurs causing the pressure to decrease. Then at point A the mitral valve opens again for the next cardiac cycle. Those skilled in the art will recognize that a similar P-V loop can be generated for the right ventricle.

The stroke volume for the ventricle is represented by the volume difference between points C and D. Changes in the preload, afterload and/or contractility can change the shape of the P-V loop and alter the stroke volume. Preferably, for most patients, it would be advantageous to have a reasonably high stroke volume without too high of pressure.

Exemplary Motion-Impedance Loop

Figure 5:
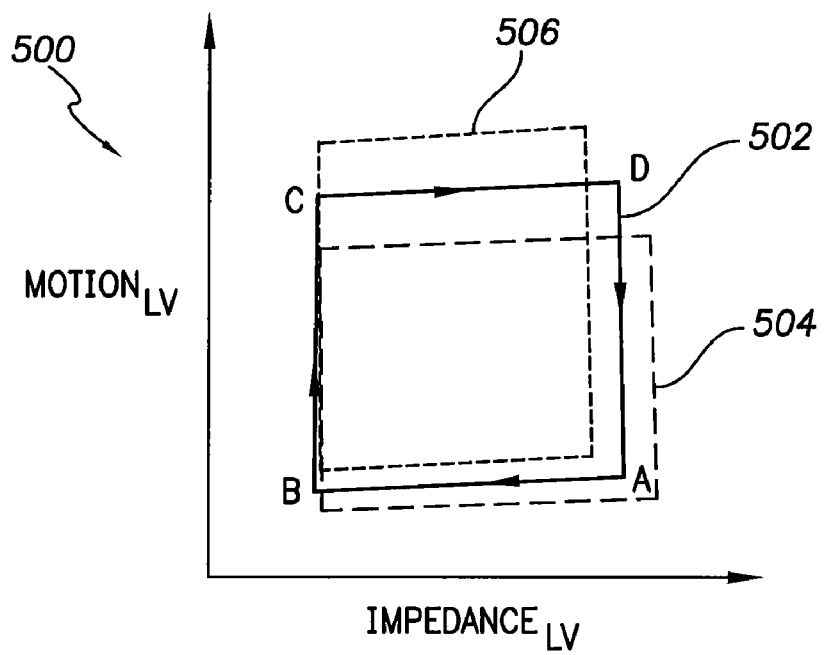
FIG. 5 is a graph depicting a pseudo P-V loop for the left ventricle, wherein pressure is replaced/represented by motion data associated with the left ventricle and volume is replaced/represented by electrical impedance data associated with the left ventricle, in accordance with certain exemplary implementations.

FIG. 5 is graph 500 depicting a simplified relationship between detected motion values associated with the LV and impedance values associated with the LV during a cardiac cycle. The motion-impedance relationship is shown here as a motion-impedance loop 502 (or pseudo P-V loop) by not considering the time element. Note that motion-impedance loop 502 includes points A–D as in FIG. 4, but in this example as indicated by the directional arrows runs in the reverse of the P-V loop 402. In this example, the motion is based on acceleration information. In other motion-impedance loops, the acceleration information may be converted to corresponding velocity and/or displacement information.

At point A the mitral valve has opened and diastolic filling starts causing the volume of blood to increase until point B is reached wherein the mitral valve closes. During this filling stage, the impedance decreases as more and more electrically conductive blood enters the chamber of the left ventricle. When the mitral valve opens at point A, the sound may be detected, for example, by accelerometer 138 (see FIG. 1B). Additional motion associated with the rapid inflow of blood from the left atrium and/or the ventricles relaxation and distensibility may also be detected. However, the motion (here, acceleration) will basically remain about the same.

When isovolumic contraction occurs between points B and C, the motion changes (here, e.g., the acceleration increases) while the impedance remains about the same since the volume of blood within the chamber has not changed. At point C, the aortic valve opens and blood is ejected from the chamber. This causes the impedance to increase while the motion stays about the same. When the aortic valve closes at point D, with most of the blood ejected from the chamber, the impedance will be higher. From point D to point A, as isovolumic relaxation occurs the impedance will remain about the same, but the motion will change, in this case decreasing. Those skilled in the art will recognize that a similar motion-impedance loop can be generated for the right ventricle.

Here, the stroke volume for the ventricle is related to the impedance difference between points C and D. As before, changes in the preload, afterload and/or contractility can change the shape of the motion-impedance loop and alter the stroke volume. Two examples of such changes are represented by modified motion-impedance loops 504 and 506. In modified motion-impedance loop 504, the stoke volume has been increased and the pressure reduced as illustrated by the increase in the difference between impedance measured at points C and D and the reduction in detected acceleration, respectively. Conversely, in modified motion-impedance loop 506, the stoke volume has been decreased and the pressure increase as illustrated by the decrease in the difference between impedance measured at points C and D and the increase in detected acceleration, respectively. For many patients, loop 504 might be most advantageous, followed by loop 502 and then probably loop 506.

As can be seen, a physician can therefore make certain treatment decisions for a given patient by examining this type of pseudo P-V loop information. Additionally, in certain implementations, logic such as pseudo P-V loop generator 238 (see FIG. 2) may automatically apply/adjust stimulation therapy in an attempt to bring/maintain all or part of the motion-impedance loop information within certain desirable boundaries. Such logic may also be configured to alert the patient/physician if the ventricle/heart appears, based on the motion-impedance loop information, to be functioning outside of certain desirable boundaries.

Exemplary Motion-Impedance Loop Generating Process

Figure 6:
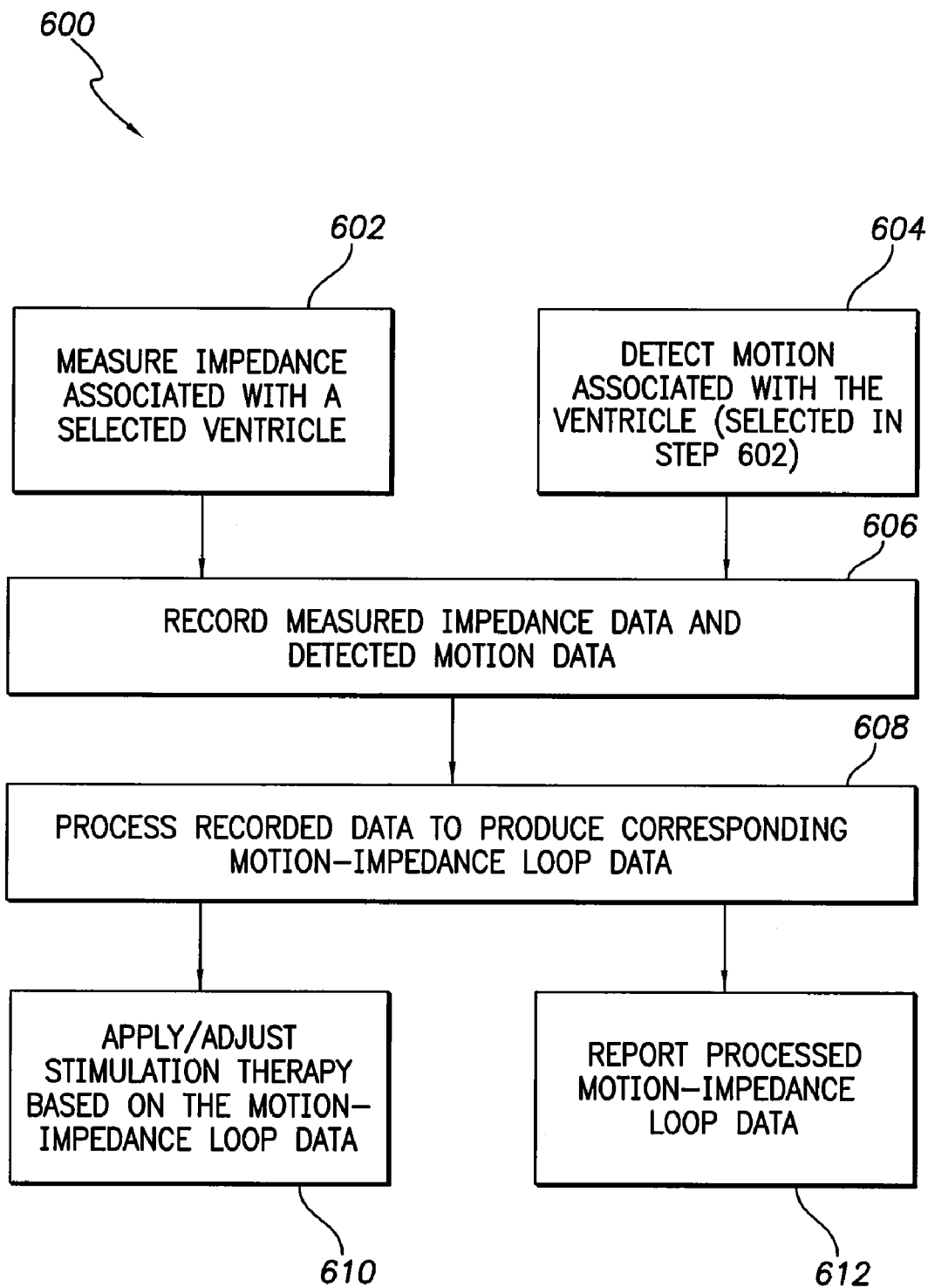
FIG. 6 is a flow chart depicting a process for generating a pseudo P-V loop, e.g., as in FIG. 5, in accordance with certain exemplary implementations.

FIG. 6 is a flow diagram illustrating a process 600 for generating pseudo P-V loop information as described in the above sections.

In step 602, impedance measurements are made for a selected ventricle during at least one cardiac cycle. Preferably, simultaneously in step 604, motion is detected in the ventricle. The measured impedance data from step 602 and the detected motion data from step 604 are recorded, e.g., stored in memory, in step 606. Data from a plurality of cardiac cycles may be stored in this manner.

In step 608, all or part of the recorded data is processed, as needed, to produce corresponding motion-impedance loop data. In step 610, stimulation therapy is applied/adjusted based on the motion-impedance loop data. In step 612, the motion-impedance loop data is reported out for further processing and/or consideration. In certain implementations, steps 610 and 612 both occur, while in other implementations either step 610 or step 612 occurs.

Exemplary Pressure-Impedance Loop

As mentioned previously, a lead may include a pressure sensor. Consequently, if a lead is placed in a targeted ventricle for chronic treatment which does include a pressure sensor, then the above techniques may be modified to take advantage of the available pressure sensor information. Thus, there would be no need to substitute motion data for pressure data in the resulting pseudo P-V loop information.

Currently, such techniques are usually only applied to the right ventricle as there remains a bias against placing leads within the left ventricle for chronic treatment. Nevertheless, this is just a treatment decision to be made by the attending physician and there may be certain instances wherein a physician does place a lead in the left ventricle for chronic treatment. Thus, this additional technique may be used in either the right and/or left ventricles.

Figure 7:
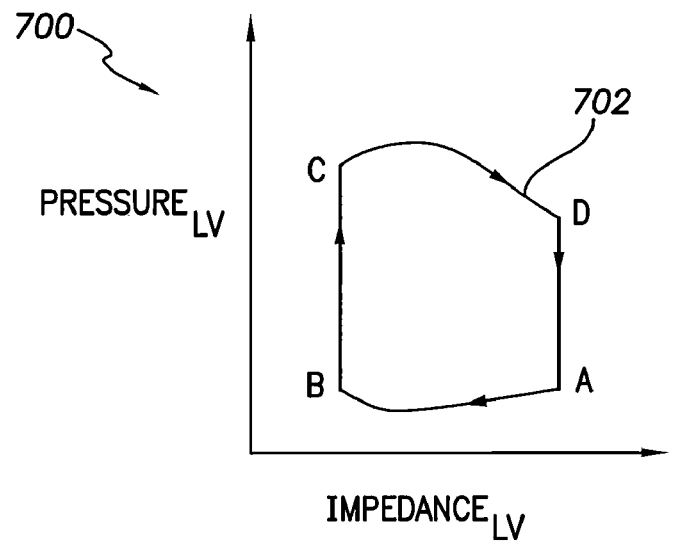
FIG. 7 is a graph depicting a pseudo P-V loop for the left ventricle, wherein volume is replaced/represented by electrical impedance data associated with the left ventricle, in accordance with certain further exemplary implementations.

With this in mind, FIG. 7 is graph 700 depicting a simplified relationship between sensed pressure values associated with the LV and impedance values associated with the LV during a cardiac cycle. The pressure-impedance relationship is shown here as a pressure-impedance loop 702 (or pseudo P-V loop) by not considering the time element. Note that pressure-impedance loop 702 includes points A–D as in FIG. 4, but in this example as indicated by the directional arrows runs in the reverse of P-V loop 402.

At point A the mitral valve has opened and diastolic filling starts causing the volume of blood to increase until point B is reached wherein the mitral valve closes. During this filling stage, the impedance decreases as more and more electrically conductive blood enters the chamber of the left ventricle. From point A to point B, the sensed pressure in the chamber changes slightly as the ventricle is filled.

When isovolumic contraction occurs between points B and C, the sensed pressure changes while the impedance remains about the same since the volume of blood within the chamber has not changed. At point C, the aortic valve opens and blood is ejected from the chamber. This causes the impedance to increase while the sensed pressure rises slightly. When the aortic valve closes at point D, with most of the blood ejected from the chamber, the impedance will be higher. From point D to point A, as isovolumic relaxation occurs the impedance will remain about the same, but the sensed pressure will decrease. Those skilled in the art will recognize that a similar pressure-impedance loop can be generated for the right ventricle.

Here, as in the previous examples, the stroke volume for the ventricle is related to the impedance difference between points C and D. Again, changes in the preload, afterload and/or contractility can change the shape (morphology) of the pressure-impedance loop and alter the stroke volume.

Exemplary Pressure-Impedance Loop Generating Process

Figure 8:
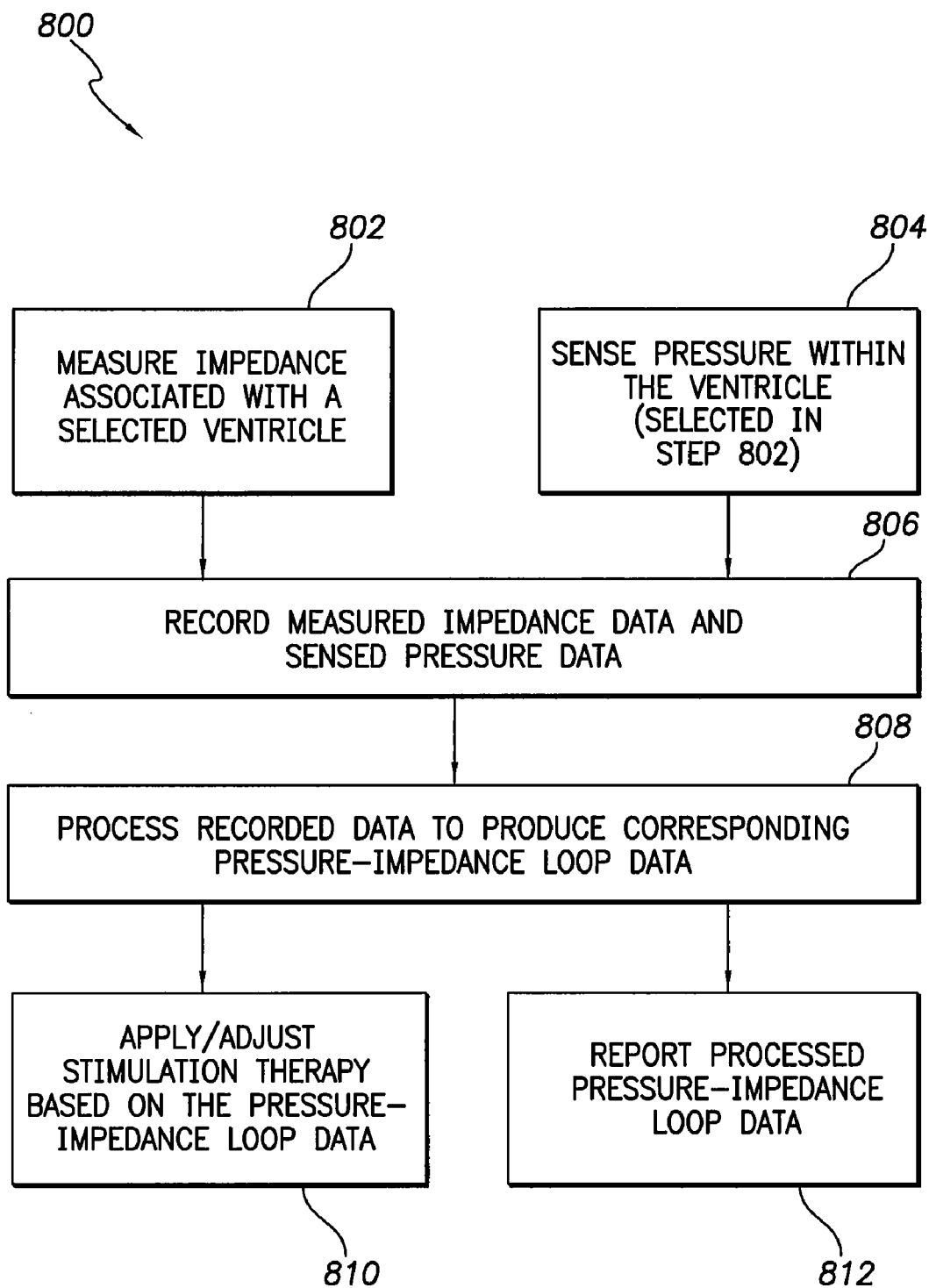
FIG. 8 is a flow chart depicting a process for generating a pseudo P-V loop, e.g., as in FIG. 7, in accordance with certain exemplary implementations.

FIG. 8 is a flow diagram illustrating a process 800 for generating pseudo P-V loop information that includes pressure and impedance information.

In step 802, impedance measurements are made for a selected ventricle during at least one cardiac cycle. Preferably, simultaneously in step 804, pressure is sensed in the ventricle. The measured impedance data from step 802 and the sensed pressured data from step 804 are recorded, e.g., stored in memory, in step 806. Data from a plurality of cardiac cycles may be stored in this manner.

In step 808, all or part of the recorded data is processed, as needed, to produce corresponding pressure-impedance loop (or curve) data. In step 810, stimulation therapy is applied/adjusted based on the pressure-impedance loop data. In step 812, at least a portion of the pressure-impedance loop data is reported out for further processing and/or consideration. In certain implementations, steps 810 and 812 both occur, while in other implementations either step 810 or step 812 occurs.

Exemplary Pressure-Plethysmogram Loop

Photoplethysmography (PPG) is a sensing technique that detects changes in vascular volume. A PPG sensor can be easily be incorporated into the header or housing of implantable cardiac devices such as ICDs and pacemakers. From a location outside the bloodstream, a PPG sensor can detect the mechanical expansion and contraction of peripheral arterioles and therefore serve as a convenient hemodynamic sensor, as described in the U.S. Pat. Nos. 6,409,675 and 6,491,639, incorporated herein by reference. The output of a PPG sensor, called a plethysmogram (pgm), serves as an accurate surrogate of arterial pulse volume and can therefore be incorporated into the construction of pseudo P-V loops.

For example, the output of the PPG sensor can serve in place of ventricular volume, and pressure can be measured directly with an intracavitary sensor, or with surrogates of pressure such as motion, as described above.

Figure 9:
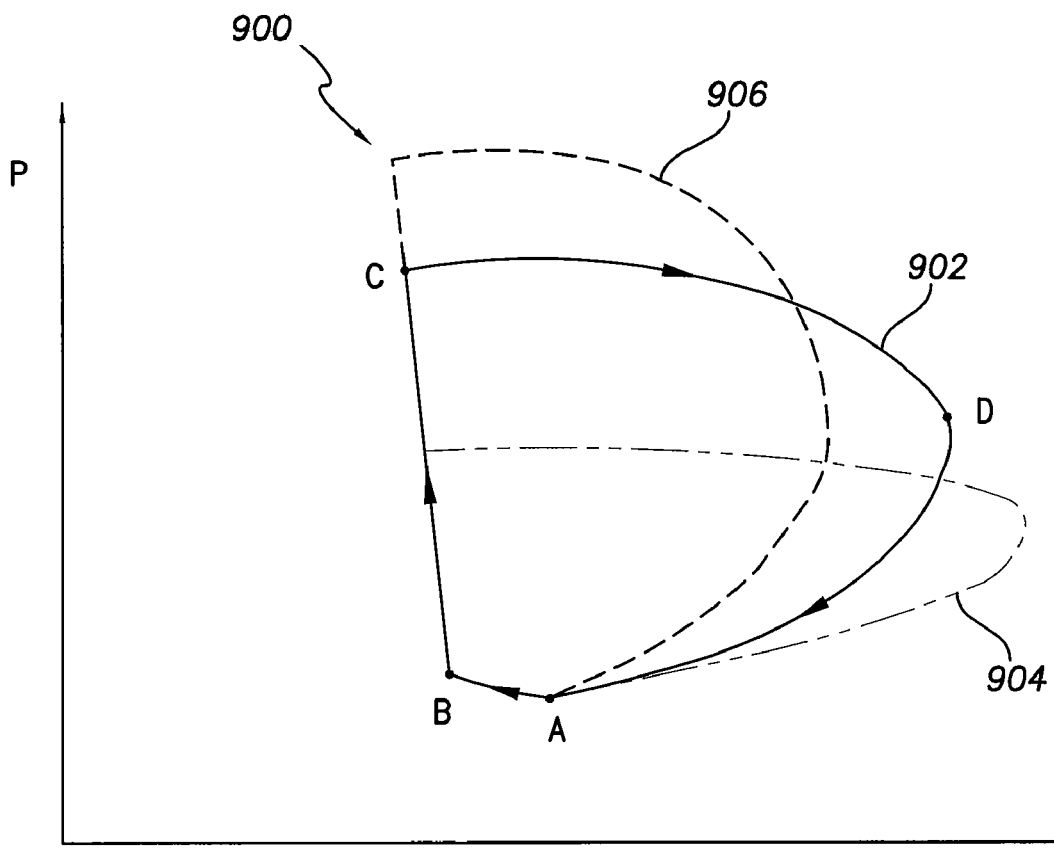
FIG. 9 is a graph depicting a simplified relationship between pressure values associated with the LV and plethysmogram values associated with volume ejected from the LV.

FIG. 9 is a graph 900 depicting a simplified relationship between pressure values associated with the LV and plethysmogram values associated with volume ejected from the LV, as measured by peripheral arteriolar volume expansion using PPG. A time delay exists between ejection of blood from the LV and arrival of the volume pulse at the periphery. This can be compensated for in the construction of the pseudo P-V loop by advancing the recorded plethysmogram in time relative to the recorded motion or pressure signal, though this step is not necessary. The pressure-plethysmogram relationship is shown here as a pressure-plethysmogram loop 902 (or pseudo P-V loop) but not considering the time element. Note that pressure-plethysmogram loop 902 includes points A–D as in FIG. 4, but in this example as indicated by the directional arrows runs in the reverse of the P-V loop 402. In addition, points A and B of the original P-V loop 402 are mapped to the same location or nearly the same location in the pseudo P-V loop 902. This is because the plethysmogram measures ejected blood volume rather than ventricular volume.

At point A the mitral valve has opened and diastolic filling starts and causes LV expansion until point B is reached wherein the mitral valve closes. However, the plethysmogram does not detect this filling since it only responds to changes in peripheral blood volume. Points A and B of the conventional P-V loop occur at the same place in this pseudo P-V loop. More precisely, point B will be offset slightly from A toward smaller plethysmogram values due to the small amount of arterial volume reduction that occurs at the periphery during this time.

When isovolumic contraction occurs between points B and C, the pressure increases while the plethysmogram remains essentially unchanged, or more precisely, attained slightly smaller values since diastolic contraction continues at the periphery during isovolumic contraction. At point C, the aortic valve opens and blood is ejected from the chamber. This causes the peripheral volume to increase (assuming the time delay has been compensated for) as the pressure stays about the same. When the aortic valve closes at point D, with most of the blood ejected from the chamber, the pressure will initially be higher but it will rapidly decreased to point A as isovolumic relaxation occurs. Those skilled in the art will recognize that a similar pressure-plethysmogram loop can be generated for the right ventricle, wherein the pressure represents the right ventricular pressure and plethysmogram represents the peripheral volume.

Here, the stroke volume for the ventricle is related to the volume differences between points C and D. As before, changes in the preload, afterload and/or contractility can change the shape of the pressure-plethysmogram loop and alter the stroke volume. Two examples of such changes are represented by modified pressure-plethysmogram loops 904 and 906 (both of which are shown in phantom). In modified pressure-plethysmogram loop 904, the stroke volume has been increased and the pressure reduced as illustrated by the increase in the difference between plethysmogram measurements at points C and D and the reduction in measured pressure. Conversely, in modified pressure-plethysmogram loop 906, the stroke volume has been decreased and the pressure increased. For many patients, loop 904 might be most advantageous, followed by loop 902 and then loop 906.

As can be seen, a physician can therefore make certain treatment decisions for a given patient by examining this type of pseudo P-V loop information. Additionally, in certain implementations, logic such as pseudo P-V loop generator 238 (see FIG. 2) may automatically apply/adjust stimulation therapy in an attempt to bring/maintain all or part of the pressure-plethysmogram loop information within certain desirable boundaries. Such logic may also be configured to alert the patient and/or physician if the heart appears, based on the pressure-plethysmogram loop information, to be functioning outside asserts desirable boundaries.

Other approaches incorporating PPG are of course possible, for example, motion can be used in place of pressure values as described above. In addition, time derivatives of the plethysmogram may be used, for example, in the construction of pseudo P-V loops using motion and the first time derivative of the plethysmogram. In yet another alternative, a pseudo P-V loop can be constructed entirely from PPG data, for example, by combining the plethysmogram and the time derivative of the plethysmogram, with the time derivative of the plethysmogram acting as a surrogate for a pressure signal. This has the advantage of not requiring auxiliary sensors such as pressure, impedance, or motion sensors.

Exemplary Pressure-Photoplethysmography Loop

Figure 10:
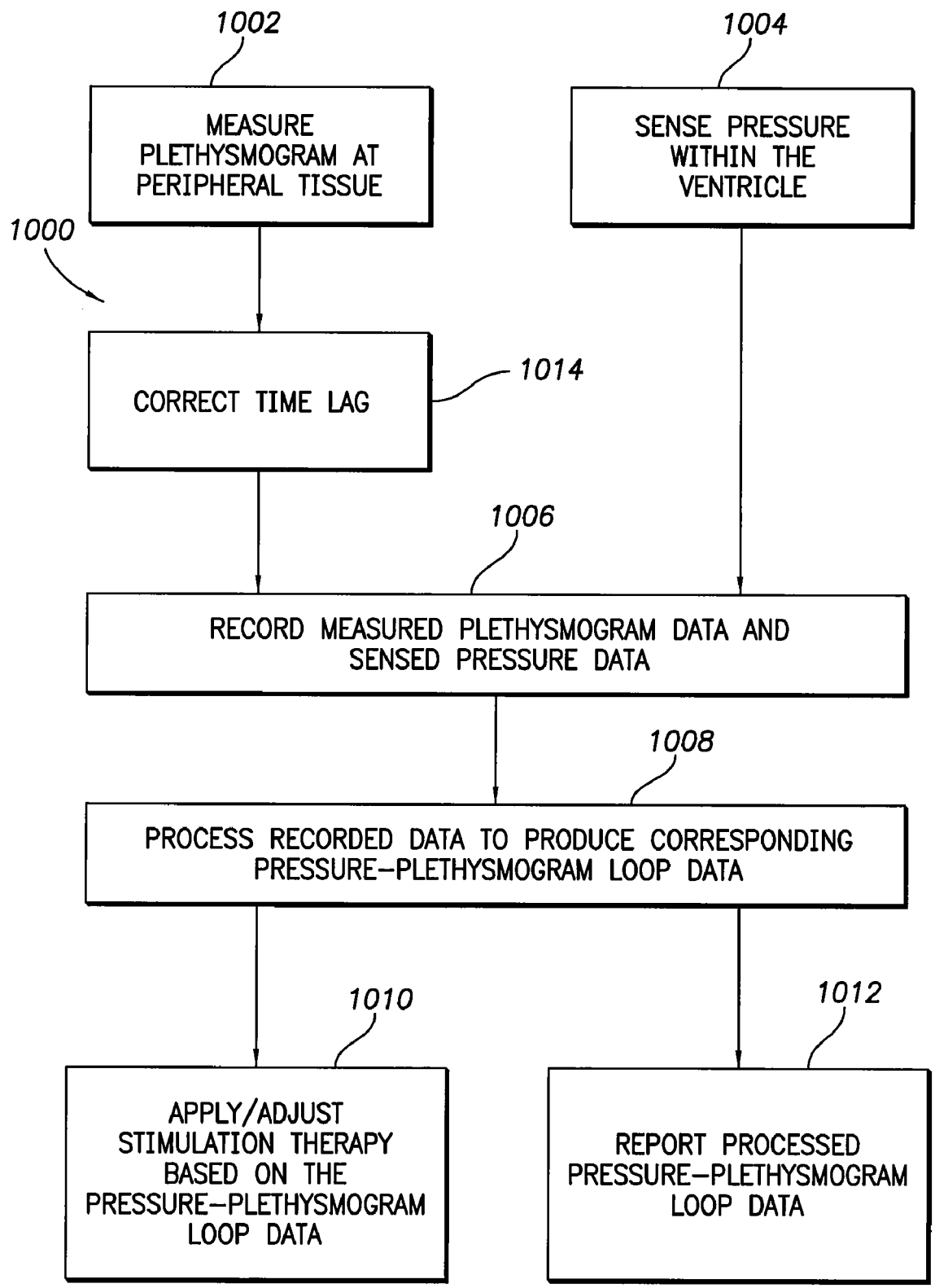
FIG. 10 is a flow chart depicting a process for generating a pseudo P-V loop, in accordance with certain exemplary implementations.

FIG. 10 is a flow diagram illustrating one illustrative embodiment of a process 1000 for generating pseudo P-V loop information as described in the above sections.

In Step 1002, plethysmogram measurements are made at the peripheral vasculature during at least one cardiac cycle. Preferably, simultaneously in step 1004, pressure is sensed in the ventricle. Optionally, at step 1014, the time delay of the PPG data is corrected. For example, the plethysmogram can be advanced in time by an amount equal to the time between the ventricular paced or sensed event and the onset of the systolic expansion in the peripheral arterioles. The measured plethysmogram and pressure data are recorded, e.g., stored in memory, in step 1006. Data from a plurality of cardiac cycles may be stored in this matter.

In step 1008, all or part of the recorded data is processed, as needed, to produce corresponding pressure-plethysmogram loop (or curve) data. In step 1010, stimulation therapy is applied/adjusted based on the pressure-plethysmogram loop data. In step 1012, at least a portion of the pressure-plethysmogram loop data is reported out for further processing and/or consideration. In certain implementations, steps 1010 and 1012 both occur, while in other implementations either step 1010 or step 1012 occurs.

CONCLUSION

Although exemplary methods and apparatuses have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and apparatuses.

What is claimed is:

1. A method for use with an implantable cardiac stimulation device, the method comprising:
   collecting plethysmogram data from a location outside the bloodstream during at least one cardiac cycle;
   determining ventricular pressure data for the at least one cardiac cycle; and
   processing the plethysmogram data as a function of the pressure data to produce data corresponding to a ventricular contraction loop.

2. The method as recited in claim 1, further comprising:
   applying stimulation therapy to at least one ventricle based on the data corresponding to a ventricular contraction loop.

3. The method as recited in claim 1, further comprising:
   transmitting the data corresponding to a ventricular contraction loop to at least one external device.

4. The method as recited in claim 2, further comprising:
   determining boundary values as defined by the data corresponding to a ventricular contraction loop for the at least one cardiac cycle.

5. The method as recited in claim 4, further comprising:
   adjusting the stimulation therapy such that subsequent boundary values fall within a predetermined range of acceptable boundary values.

6. The method as recited in claim 1, wherein:
   processing the plethysmogram data as a function of the pressure data comprises processing the plethysmogram data to derive a metric of ventricular volume which is then processed as a function of the pressure data to produce data corresponding to a ventricular contraction loop.

7. The method as recited in claim 1, wherein determining ventricular pressure data for the at least one cardiac cycle comprises:
   collecting ventricular motion data during the at least one cardiac cycle, and processing the ventricular motion data to derive a metric of ventricular pressure.

8. The method as recited in claim 1, wherein determining ventricular pressure data for the at least one cardiac cycle comprises:
   collecting ventricular pressure data from within the ventricle during the at least one cardiac cycle.

9. The method as recited in claim 1, wherein determining ventricular pressure data for the at least one cardiac cycle comprises computing a derivative of the plethysmogram data collected during the at least one cardiac cycle to derive a metric of ventricular pressure.

10. An implantable cardiac stimulation device comprising:
    means for collecting plethysmogram data from a location outside the bloodstream during at least one cardiac cycle;
    means for determining ventricular pressure data for the at least one cardiac cycle; and
    means for processing the plethysmogram data as a function of the pressure data to produce data corresponding to a ventricular contraction loop.

11. The implantable cardiac stimulation device as recited in claim 10, further comprising:
    means for applying stimulation therapy to at least one ventricle based on the data corresponding to a ventricular contraction loop.

12. The implantable cardiac stimulation device as recited in claim 10, further comprising:
    means for transmitting the data corresponding to a ventricular contraction loop to at least one external device.

13. The implantable cardiac stimulation device as recited in claim 10, and further comprising:
    means for determining boundary values as defined by the data corresponding to a ventricular contraction loop for the at least one cardiac cycle.

14. The implantable cardiac stimulation device as recited in claim 13, further comprising:
    means for adjusting the stimulation therapy such that subsequent boundary values fall within a predetermined range of acceptable boundary values.

15. The implantable cardiac stimulation device as recited in claim 10, wherein:

the means for processing the plethysmogram data as a function of the pressure data comprises means for processing the plethysmogram data to derive a metric of ventricular volume which is then processed as a function of the pressure data to produce data corresponding to a ventricular contraction loop.

16. The implantable cardiac stimulation device as recited in claim 10, and further comprising wherein means for determining ventricular pressure data for the at least one cardiac cycle comprises:

means for collecting ventricular motion data during the at least one cardiac cycle, and processing the ventricular motion data to derive a metric of ventricular pressure.

17. The implantable cardiac stimulation device as recited in claim 10, and further comprising wherein determining ventricular pressure data for the at least one cardiac cycle comprises:

means for collecting ventricular pressure data from within the ventricle during the at least one cardiac cycle.

18. The implantable cardiac stimulation device as recited in claim 10, wherein the means for determining ventricular pressure data for the at least one cardiac cycle comprises means for computing a derivative of the plethysmogram data collected during the at least one cardiac cycle to derive a metric of ventricular pressure.

* * * * *